US011395863B2

(12) United States Patent
Oyama et al.

(10) Patent No.: US 11,395,863 B2
(45) Date of Patent: Jul. 26, 2022

(54) MODIFICATION METHOD FOR SHEET-SHAPED CELL CULTURE

(71) Applicant: TERUMO KABUSHIKI KAISHA, Tokyo (JP)

(72) Inventors: Kenji Oyama, Kanagawa (JP); Ryohei Takeuchi, Kanagawa (JP); Toshikazu Takeuchi, Kanagawa (JP)

(73) Assignee: TERUMO KABUSHIKI KAISHA, Tokyo (JP)

(*) Notice: Subject to any disclaimer, the term of this patent is extended or adjusted under 35 U.S.C. 154(b) by 731 days.

(21) Appl. No.: 16/188,630

(22) Filed: Nov. 13, 2018

(65) Prior Publication Data

US 2019/0076576 A1    Mar. 14, 2019

Related U.S. Application Data

(63) Continuation of application No. PCT/JP2017/039476, filed on Nov. 1, 2017.

(30) Foreign Application Priority Data

Nov. 1, 2016 (JP) .............................. JP2016-214224

(51) Int. Cl.
A61L 27/38 (2006.01)
C12N 5/00 (2006.01)
C12N 5/077 (2010.01)
C12N 1/00 (2006.01)

(52) U.S. Cl.
CPC ............ A61L 27/3804 (2013.01); C12N 1/00 (2013.01); C12N 5/0081 (2013.01); C12N 5/0087 (2013.01); C12N 5/0656 (2013.01); C12N 5/0658 (2013.01)

(58) Field of Classification Search
CPC .. A61L 27/3804; C12N 5/0658; C12N 5/0656
See application file for complete search history.

(56) References Cited

U.S. PATENT DOCUMENTS

| 9,737,636 | B2 | 8/2017 | Oohashi et al. |
| 2003/0211141 | A1 | 11/2003 | LeBaron et al. |
| 2007/0092492 | A1 | 4/2007 | Matsuda et al. |
| 2009/0275132 | A1 | 11/2009 | Hattori et al. |
| 2010/0189699 | A1 | 7/2010 | Hattori et al. |
| 2016/0067284 | A1 | 3/2016 | Sakamoto et al. |
| 2016/0122716 | A1 | 5/2016 | Yamanaka et al. |
| 2018/0245047 | A1 | 8/2018 | Matsuura et al. |

FOREIGN PATENT DOCUMENTS

| CN | 101374942 A | 2/2009 |
| CN | 101711277 A | 5/2010 |
| CN | 102191218 A | 9/2011 |
| CN | 105229145 A | 1/2016 |
| EP | 2 682 134 A1 | 1/2014 |
| EP | 3 064 578 A1 | 9/2016 |
| EP | 3 219 790 A1 | 9/2017 |
| JP | 2007-089442 A | 4/2007 |
| JP | 2007-528755 A | 10/2007 |
| JP | 2010-081829 A | 4/2010 |
| JP | 2010-099052 A | 5/2010 |
| JP | 2010-226991 A | 10/2010 |
| JP | 2011-110368 A | 6/2011 |
| JP | 2012-039906 A | 3/2012 |
| JP | 2016-052269 A | 4/2016 |
| JP | 2016-052270 A | 4/2016 |
| WO | 2003012076 A2 | 2/2003 |
| WO | 2014-185358 A1 | 11/2014 |
| WO | 2017/038562 A1 | 3/2017 |

OTHER PUBLICATIONS

Kobayashi et al. Fibroblast sheets co-cultured with endothelial progenitor cells improve cardiac function of infarcted hearts, 2008. J Artif Organs 11:141-147 (Year: 2008).*
Shimizu et al. Fabrication of Pulsatile Cardiac Tissue Grafts Using a Novel 3-Dimensional Cell Sheet Manipulation Technique and Temperature-Responsive Cell Culture Surfaces 2002. Circ Res. 90:e40-e48 (Year: 2002).*
Hata et al. Grafted skeletal myoblast sheets attenuate myocardial remodeling in pacing-induced canine heart failure model 2006. J Thorac Cardiovasc Surg 132(4):918-24 (Year: 2006).*
Malhorta Current developments in interim transport (storage) media in dentistry: an update 2011. British Dental Journal 211: 29-33 (Year: 2011).*
Hiltz Vitality of human lip fibroblasts in milk, Hanks balanced Salt solution and Viaspan storage media 1991 Dental Traumology 7(2) (Year: 1991).*
Hiltz et al. Vitality of human lip Fibroblasts in milk, Hanks balanced salt solution and Viaspan storage media 1991; Endod Dent Traumatol 7: 69-72 (Year: 1991).*
Iyer et al., "Chitosan Selectively Promotes Adhesion of Myoblasts over Fibroblasts: Effects of Chitosan on Myoblasts and Fibroblasts", Journal of Biomedical Materials Research, Part A, (Jun. 1, 2015), vol. 103, No. 6, pp. 1899-1906.
Kino-Oka et al., "Preferential Growth of Skeletal Myoblasts and Fibroblasts in Co-Culture on a Dendrimer-Immobilized Surface", Journal of Bioscience and Bioengineering, (Jan. 1, 2013), vol. 115, No. 1, pp. 96-99.
The extended European Search Report dated Jun. 17, 2019, by the European Patent Office in corresponding European Patent Application No. 17867551.8-1120. (8 pages).
Haraguchi, et al., Concise Review: Cell Therapy and Tissue Engineering for Cardiovascular Disease, Stem Cells Translational Medicine, Jan. 26, 2012, pp. 136-141, 1.

(Continued)

Primary Examiner — Taeyoon Kim
Assistant Examiner — Alexandra F Connors
(74) Attorney, Agent, or Firm — Buchanan Ingersoll & Rooney PC

(57) ABSTRACT

A method is disclosed for modifying a sheet-shaped cell culture containing at least two types of cells. The method includes soaking the sheet-shaped cell culture in a low nutrient isotonic solution; and changing a content ratio of the at least two cell types constituting the sheet-shaped cell culture.

24 Claims, 1 Drawing Sheet

(56) References Cited

OTHER PUBLICATIONS

Miki, et al., Efficient Detection and Purification of Cell Populations Using Synthetic MicroRNA Switches, Cell Stem Cell, Cell Press, Jun. 4, 2015, pp. 699-711, 16, http://dx.doi.org/10.1016/j.stem.2015.04.005, Elsevier Inc.

Reis, et al., Effect of different storage media on root dentine composition and viability of fibroblasts evaluated by several assay methods, International Endodontic Journal, Jan. 20, 2017, 2 pages, First published Dec. 16, 2016 at https://doi.org/10.1111/iej.12739.

Sawa, et al., Tissue engineered myoblast sheets improved cardiac function sufficiently to discontinue LVAS in a patient with DCM: report of a case, Surg Today, 2012, pp. 181-184, 42, DOI 10.1007/S00595-011-0106-4; Springer, Published online Dec. 27, 2011.

International Search Report and Written Opinion issued in corresponding International Patent Application No. PCT/JP2017/039476, Jan. 3, 2018, 11 pages.

An English Translation of the International Search Report (Form PCT/ISA/210) and the Written Opinion of the International Searching Authority (Form PCT/ISA/237) dated Jan. 30, 2018, by the Japanese Patent Office in corresponding International Application No. PCT/JP2017/039476. (7 pages).

Gong et al., "A Tutorial in Radiomedical Experiments," Atomic Energy Press, (Feb. 28, 2009), p. 174 (3 pages).

Wang et al., "Isolation, Identification and Induced Differentiation of Bovine Skeletal Muscle Satellite Cells," Chinese Animal Husbandry and Veterinary Medicine, (Jul. 31, 2014), vol. 41, No. 7, pp. 142-147.

Office Action (The First Office Action) dated May 6, 2021, by the State Intellectual Property Office of People's Republic of China in corresponding Chinese Patent Application No. 201780031342.1 and an English Translation of the Office Action. (27 pages).

English Translation of the Office Action (Notice of Reasons for Refusal) dated Jun. 21, 2018, by the Japanese Patent Office in corresponding Japanese Patent Application No. 2018-521436. (4 pages).

Office Action (Decision of Refusal), with English Translation, dated Feb. 7, 2022, by the Japanese Patent Office in corresponding Japanese Patent Application No. 2018-199652 (10 pages).

Office Action (The Third Office Action) dated Mar. 18, 2022, by the State Intellectual Property Office of People's Republic of China in corresponding Chinese Patent Application No. 201780031342.1 and an English Translation of the Office Action. (11 pages).

* cited by examiner

MODIFICATION METHOD FOR
SHEET-SHAPED CELL CULTURE

CROSS-REFERENCES TO RELATED
APPLICATIONS

This application is a continuation of International Application No. PCT/JP2017/039476 filed on Nov. 1, 2017, which claims priority to Japanese Application No. 2016-214224 filed on Nov. 1, 2016, the entire content of both of which is incorporated herein by reference.

TECHNICAL FIELD

The present disclosure generally relates to methods for modifying a sheet-shaped-state cell culture and methods for producing a sheet-shaped cell culture.

BACKGROUND DISCUSSION

In recent years, various cells are being transplanted in order to repair damaged tissues and the like. For example, the use of fetal cardiac muscle cells, skeletal myoblasts, mesenchymal stem cells, heart stem cells, and ES cells are being used in order to repair cardiac muscle tissues damaged, for example, by ischemic cardiac heart disease, such as angina pectoris and cardiac infarction, dilated cardiomyopathy, and the like (Haraguchi et al., Stem Cells, Transl Med. 2012 February; 1 (2): 136-41, and Sawa et al., Surg Today. 2012 January; 42 (2): 181-4).

As part of these attempts, cell structures formed using a scaffold and sheet-shaped cell cultures with cells formed in the shape of a sheet have been developed. (JP 2007-528755T, and Sawa et al., Surg Today. 2012 January; 42 (2): 181-4).

As for applications of sheet-shaped cell cultures to medical treatments, research includes the use of a cultured epidermis sheet for skin damage due to a scald or the like, the use of a sheet-shaped corneal epithelium cell culture for a corneal damage, the use of a sheet-shaped oral mucosa cell culture for endoscopic esophageal cancer resection, and the like, and some of the research has been advanced to clinical application stages.

The medicinal effects of general medicines, such as medicines with a low molecular weight compounds contained as an active ingredients can be modified by chemically modifying the active ingredients, adding an excipient, or changing the dosage forms, or in a similar manner. Such modifications can, however, be hardly made on the medicinal effects of a medicine containing a sheet-shaped cell culture, as opposed to such general medicines. Thus, upon production of a medicinal composition containing a sheet-shaped cell culture, the preparation of sheet-shaped cell culture of higher-quality is required in the stage of formation of the sheet-shaped cell culture. To this end, attempts have been conducted (for example, JP 2010-226991A, etc.) Meanwhile, there are no reports regarding a technique of modifying a sheet-shaped formed cell culture further after the formation into a sheet.

SUMMARY

A method is disclosed for modifying a sheet-shaped cell culture by changing the content ratio (i.e., ratio of cells) of at least two types of cells, which constitute the sheet-shaped cell culture after the sheet-shaped cell culture is formed.

In the case of a sheet-shaped cell culture for use in regenerative therapy or the like, cells other than a desired type of cells are considered to be impurities, and thus the higher the purity of the desired type of cells, the more preferred. However, such a sheet-shaped cell culture for use in transplantation is produced preferably with autologous cells, which have been prepared from pieces of tissue collected from a recipient, in order to reduce rejection reactions or for a like purpose, so that the cells other than the desired type of cells cannot be completely removed in many instances. Meanwhile, as described above, there are no reports regarding the method of changing the purity of cells after a sheet-shaped cell culture is produced. Thus, it has heretofore been a practice to increase the purity of a desired type of cells by producing a sheet-shaped cell culture from autologous cells which have been prepared with as high as a purity as possible.

While proceeding with research for a sheet-shaped cell culture of skeletal myoblasts, the present inventors came across a new finding that soaking (dipping, or immersing) of a produced sheet-shaped cell culture of skeletal myoblasts in Hanks' balanced salt solution (HBSS) decreases the content ratio of mixed fibroblasts but increases the content ratio of skeletal myoblasts, as a desired type of cells. The present inventors conducted a series of research based on that finding, leading to the completion of the present disclosure.

Described specifically, the present disclosure provides the followings.

<1> A method for modifying a sheet-shaped cell culture containing at least two types of cells, including: soaking the sheet-shaped cell in a low nutrient isotonic solution, whereby a content ratio of the cell types constituting the sheet-shaped cell culture is changed.

<2> The method as described above in <1>, in which the sheet-shaped cell culture contains skeletal myoblasts and fibroblasts.

<3> The method as described above in <2>, in which the modification is to reduce a content of fibroblasts.

<4> The method as described above in any one of <1> to <3>, in which the sheet-shaped cell culture is a sheet-shaped cell culture.

<5> The method as described above in <4>, in which the sheet-shaped cell culture has been separated from a culture substrate.

<6> The method as described above in <5>, in which the sheet-shaped cell culture has contracted upon the separation.

<7> The method as described above in <5> or <6>, in which the sheet-shaped cell culture has an area of not less than 6 $cm^2$ after the separation.

<8> The method as described above in any one of <4> to <7>, in which the sheet-shaped cell culture comprises a plurality of single layer sheet-shaped cell cultures stacked together.

<9> The method as described above in any one of <1> to <8>, in which the low nutrient isotonic solution is Hanks' balanced salt solution.

<10> The method as described above in any one of <1> to <9>, in which the soaking is conducted for 24 hours to 150 hours.

<11> The method as described above in any one of <1> to <10>, in which the soaking is conducted at 2° C. to 8° C.

<12> A method for producing a sheet-shaped cell culture, including the following steps (a), (b), and (c):

(a) seeding a cell population, which contains two or more types of cells on a culture substrate at a density capable of forming a sheet-shaped cell culture without substantial proliferation;

(b) subjecting the seeded cell population to sheet-forming culture to form the sheet-shaped cell culture; and (c) soaking the formed sheet-shaped cell culture in a low nutrient isotonic solution.

<13> The method as described above in <12>, including, before the step (c), the following step (c'):

(c') separating the formed sheet-shaped cell culture.

<14> The method as described above in <12>, including, after the step (c), the following step (c'):

(c') separating the formed sheet-shaped cell culture.

<15> The method as described above in <13> or <14>, in which in the step (c') the sheet-shaped cell culture contracts upon the separation.

<16> The method as described above in any one of <13> to <15>, in which the separated sheet-shaped cell culture has an area of not less than 6 cm$^2$.

<17> The method as described above in any one of <13> to <16>, further including, after the step (c'), the following step (c"):

(c") stacking together a plurality of separated sheet-shaped cell cultures as defined in the corresponding one of <13> to <16>.

<18> A method for producing a sheet-shaped cell culture, including the following steps (a), (b), (c), and (d):

(a) seeding a cell population, which contains desired types of cells, on a culture substrate at a density capable of forming a sheet-shaped cell culture without substantial proliferation;

(b) subjecting the seeded cell population to sheet-forming culture to form a sheet-shaped cell culture;

(c) separating the formed sheet-shaped cell culture; and (d) soaking the separated sheet-shaped cell culture in a low nutrient isotonic solution.

According to the present disclosure, it is possible, after formation of a sheet-shaped cell culture, for example, in the shape of a sheet to further modify the sheet-shaped cell culture so as to improve the quality of the sheet-shaped cell culture. Therefore, it is possible to further improve the quality of a sheet-shaped cell culture produced by an existing method so that a sheet-shaped cell culture, which has heretofore been considered to be insufficient in quality, can be improved to sufficient quality after preparation. Thus, elimination of wasting of time or materials can be realized, thereby reducing risks to recipients. In addition, modification procedure of the sheet-shaped cell culture can be relatively simple, and thus can be widely used for various sheet-shaped cell cultures.

DETAILED DESCRIPTION

Figure 1:
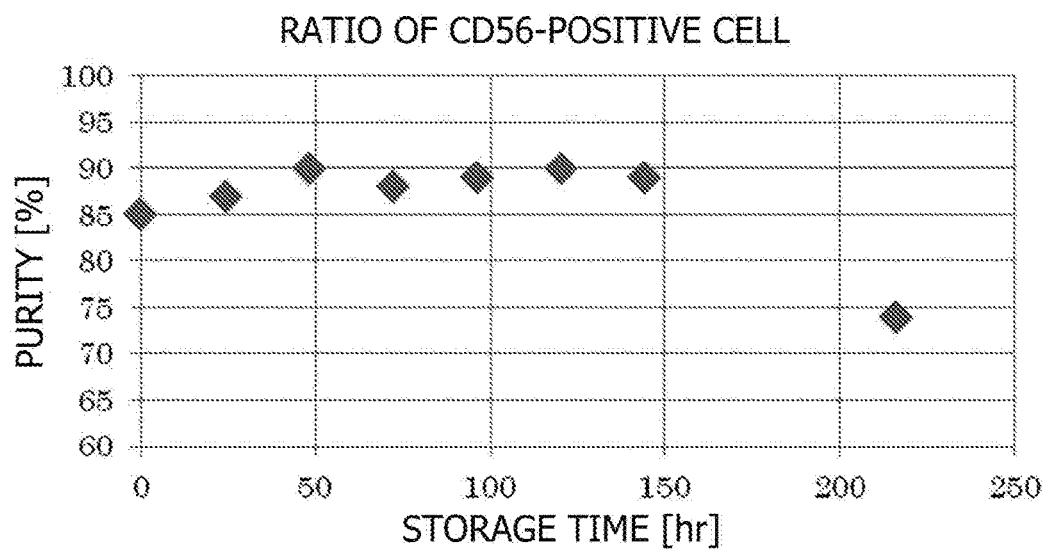
FIG. 1 is a graph depicting changes in the purity of skeletal myoblasts at every 24th hour when a sheet-shaped cell culture containing human skeletal myoblasts and human fibroblasts was soaked in HBSS (+) under refrigerated conditions. In the figure, CD56-positive cells refer to skeletal myoblasts. The purity started increasing from the start of soaking, and reached approximately 90% in approximately 48 hours. Then, the purity remained effectively until approximately the sixth day after the start of soaking.

Unless otherwise defined herein, all the technical terms and scientific terms used in this description have the same meanings as generally understood by those skilled in the art. All the patents, applications, published applications and other publications referred to herein should be cited by reference in their entirety. In addition, if any contradiction arises between publications referred to in this description and recitations in this description, the recitations in this description supersede.

In the present disclosure, the expression "modify a sheet-shaped cell culture" means to change the structure, function, characteristics, and/or the like of the sheet-shaped cell culture, as compared with those before the treatment. The term "modify" may include changing in a worsening direction, but herein preferably means to change in an improving direction, namely, means to change so that the sheet-shaped cell culture is prepared (or modified) to be more suited for the application purpose of the sheet-shaped cell culture.

In the present disclosure, the term "sheet-shaped cell culture" means a cell culture in which cells have been formed in adhesion with other cells or a substrate. Cells may be linked together directly (including those linked together via cellular elements, such as adhesion molecules) and/or linked together via an intervening (cell-cell matrix) substance. Examples of the intervening substance may include an extracellular matrices or the like, although the intervening substance is not particularly limited insofar as the intervening substance can at least physically (mechanically) link cells together. The intervening substance is preferably a substance derived from cells, in particular, a substance derived from cells constituting the cell culture. Although the cells are linked together at least physically (mechanically), they may be further linked together functionally, for example, chemically or electrically. The term "sheet-shaped cell culture" can include a sheet-shaped cell culture in a state that cells are in adhesion with a substrate, a cell culture in a state that cells are liberated from any substrate, but in adhesion with one another, and a cell culture in a state that cells are in adhesion with a substrate and are also in adhesion with one another. Examples of the sheet-shaped cell culture may include, but are not limited to, a sheet-shaped cell culture, a cell aggregate, an embryoid body, a spheroid and the like, with the sheet-shaped cell culture being preferred. In an embodiment, the sheet-shaped cell culture includes a sheet-shaped cell culture in a state that cells are in adhesion with the substrate. In another embodiment, the sheet-shaped cell culture can include a cell culture in a state that cells are liberated from the substrate. Examples may include, but are not limited to, a sheet-shaped cell culture separated from a substrate, an embryoid body obtained by suspension culture, a spheroid, and the like.

In the present disclosure, the term "sheet-shaped cell culture" means cells linked together into the shape of a sheet. Cells may be linked together directly (including those inked through via cellular elements, such as adhesion molecules) and/or linked together via an intervening substance. The intervening substance is not particularly limited insofar as it is a substance having at least an ability to physically (mechanically) link cells together. Examples of the intervening substance may include extracellular matrices and the like. The intervening substance may preferably be a substance derived from cells, in particular, a substance derived from cells constituting the cell culture. Although the cells are linked at least physically (mechanically), the cells may be further linked functionally, for example, chemically or electrically. The sheet-shaped cell culture may be a culture configured with a single cell layer (single layer), or a culture configured with two or more cell layers (stacked (multilayer)

architecture, for example, two layers, three layers, four layers, five layers, six layers, and so on).

It is preferred for the sheet-shaped cell culture to include no scaffold (support). A scaffold may be used in this technical field to maintain the physical integrity of a sheet-shaped cell culture by causing adhesion of cells on the surface and/or in the inside of the scaffold. Known scaffolds, for example, include a film made of polyvinylidene difluoride (PVDF) and the like. The sheet-shaped cell culture in the present disclosure may be a culture that can maintain the physical integrity of the sheet-shaped cell culture without such a scaffold. In addition, it may be preferred for the sheet-shaped cell culture to consist of substances derived from cells constituting the cell culture and to be free of other substances.

The cells constituting the sheet-shaped cell culture, preferably the cells constituting the sheet-shaped cell culture, are not particularly limited, insofar as they can form the sheet-shaped cell culture, preferably the sheet-shaped cell culture. Examples include adhesion cells (adherent cells). Illustrative adhesion cells include adherent somatic cells (for example, cardiac muscle cells, fibroblasts, epithelium cells, endothelial cells, hepatocytes, pancreatic cells, renal cells, adrenal gland cells, human periodontal ligament cells, gingiva cells, periosteum cells, skin cells, synovial cells, cartilage cells, and the like) and stem cells (for example, myoblast cells, tissue stem cells such as heart stem cells, embryonic stem cells, pluripotent stem cells, such as iPS (induced pluripotent stem) cells, mesenchymal stem cells and the like), and so on. The somatic cells may be stem cells, in particular, cells differentiated from iPS cells (adhesion cells derived from iPS cells). As for non-limiting examples of cells constituting the sheet-shaped cell culture, there are, for example, myoblast cells (for example, skeletal myoblasts and the like), mesenchymal stem cells (for example, bone marrow, adipose tissue, peripheral blood, skin, hair root, muscular tissue, endometrium, placenta, cord blood-derived cells, and the like), cardiac muscle cells (cardiomyocyte cells), fibroblasts, heart stem cells, embryonic stem cells, iPS cells, synovial cells, cartilage cells, epithelium cells (for example, oral mucosaepithelium cells, retinal pigment epithelial cells, nasal epithelial cells, and the like), endothelial cells (for example, vascular endothelial cells and the like), hepatocytes (for example, hepatic parenchymal cells and the like), pancreatic cells (for example, islet cells and the like), renal cells, adrenal gland cells, human periodontal ligament cells, gingiva cells, periosteum cells, skin cells and the like. As for non-limiting examples of the adhesion cells derived from iPS cells, there are cardiac muscle cells (cardiomyocyte cells), fibroblasts, epithelium cells, endothelial cells, hepatocytes, pancreatic cells, renal cells, adrenal gland cells, human periodontal ligament cells, gingiva cells, periosteum cells, skin cells, synovial cells, cartilage cells and the like, all of which have been derived from iPS cells.

The cells constituting the sheet-shaped cell culture, particularly the sheet-shaped cell culture, may be derived from a desired living organism for which a medical treatment with the sheet-shaped cell culture, particularly the sheet-shaped cell culture, is feasible. Without being limited, the living organism may include, for example, human, non-human primates, dogs, cats, pigs, horses, goats, sheep, rodent animals (for example, mice, rats, hamsters, guinea pigs and the like), rabbits, and so on. In addition, the number of types of the cells constituting the sheet-shaped cell culture, particularly the sheet-shaped cell culture, is not particularly limited. In general, only a single type of cells may be included. In the present disclosure, two or more types of cells are included in the sheet-shaped cell culture with two types of cells being preferred. In the case where two or more types of cells form the sheet-shaped cell culture, for example, the content in ratio (purity) of cells the number of which is the larger may be not less than 50%, preferably not less than 60%, further preferably not less than 70%, still more preferably not less than 75% at the end of the formation time point of the sheet-shaped cell culture.

The cells forming the sheet-shaped cell culture, particularly the sheet-shaped cell culture, may be xenogeneic derived cells or allogeneic derived cells. When the sheet-shaped cell culture, particularly the sheet-shaped cell culture, is used for transplant, the term "the xenogeneic derived cells" as used herein means cells derived from a living organism different in species from the recipient. When the recipient is a human, for example, the xenogeneic derived cells can be cells derived from a monkey, a pig or the like. The term "allogeneic derived cells" means cells derived from a living organism of the same species as the recipient. When the recipient is a human, for example, the allogeneic derived cells can be human cells. The allogeneic derived cells include autologous derived cells (also referred to as host cells or autologous cells), in other words, recipient-derived cells, and also allogeneic non-host derived cells (also referred to as allogeneic cells). The autologous derived cells are preferred particularly for use in transplant, because their transplant causes no rejection reaction. However, xenogeneic derived cells and allogeneic non-host derived cells can be used. When xenogeneic derived cells or allogeneic non-host derived cells are used, an immunosuppression care may be required in order to inhibit a rejection reaction. It is to be noted that, in this description, cells other than autologous derived cells, that is, xenogeneic derived cells and allogeneic non-host derived cells may be collectively referred to as non-autologous derived cells. In an embodiment of the present disclosure, cells are autologous cells or allogeneic cells. In another embodiment of the present disclosure, cells are autologous cells. In a further embodiment of the present disclosure, cells are allogeneic cells.

A sheet-shaped cell culture can be produced by any desired known method (see, for example, JP 2007-528755T, JP 2010-226991A, JP 2010-081829A, JP 2011-110368A, or the like). A production method for producing a sheet-shaped cell culture typically includes a step of seeding cells on a culture substrate, a step of subjecting the seeded cells to sheet-forming culture, and a step of separating the formed sheet-shaped cell culture from the culture substrate, but not particularly restricted. In accordance with an exemplary embodiment, it is possible to conduct, before the step of seeding the cells on the culture substrate, a step of freezing the cells and a step of thawing the cells. Further, it is possible to perform a step of washing the cells, after the step of thawing the cells. Each of these steps can be implemented by any desired known method suited for producing the sheet-shaped cell culture. The production method of the present disclosure may include a step of producing the sheet-shaped cell culture. In this case, the step of producing the sheet-shaped cell culture may include, as a sub step on sub steps, one or more of the steps in the methods for producing the above-described sheet-shaped cell culture. In an embodiment, no step is included to proliferate cells after the step of thawing cells and before the step of seeding cells on a culture substrate.

The term "isotonic" means a state in which two kinds of liquids are equivalent in osmotic pressure. However, the term "isotonic" as used herein means "physiologically isotonic" unless specified otherwise, and means to have an osmotic pressure equivalent to that of a physiological liquid, such as an intracellular fluid and blood. Thus, in the present disclosure, the term "isotonic solution" has the same meaning as the term "physiologically isotonic solution" unless specified otherwise, and means a liquid having an osmotic pressure equivalent to that of a physiological liquid, such as an intracellular fluid and blood. Examples of the isotonic solution may include, but are not limited to, Hanks' balanced salt solution, saline, phosphate-buffered physiological saline, ringer solution, basal medium and the like.

In the present disclosure, the term "low nutrient" or "low nutrient state" means conditions under which the cell count of a cell population placed under the conditions remains with neither proliferation nor extinction for a predetermined period, in other words, conditions under which the cell count remains substantially unchanged for a predetermined period. The expression "the cell count remains substantially unchanged" means that there is no substantial difference between a cell count A at a time point and a cell count B at another time point after a lapse of a predetermined period from the former time point. Described specifically, "the cell count remains substantially unchanged" means several cases where the cell count A is approximately 70%, approximately 80%, approximately 90%, approximately 95%, approximately 100%, approximately 105%, approximately 110%, approximately 120%, approximately 130% or the like of the cell count B, for example. These two time points may be arbitrarily selected. However, when culturing is conducted under normal culturing conditions, it is preferred to leave an interval to such an extent that proliferation of cells can be confirmed. Such an interval may be, for example, three days, four days, five days, six days, seven days or the like.

The low nutrient state may be attained under various conditions. Any of those skilled in the art can appropriately create a low nutrient state in accordance with desired cells. The requirement or requirements of a low nutrient state may typically include that energy required for the life support of cells can be supplied, that elements required for cell division is lacked, and/or the like, for example. Specific examples may include an environment where energy, such as a sugar, required for metabolism can be supplied, an environment where an essential amino acid required for cell division cannot be supplied, and/or the like.

In an embodiment, "low nutrient" means a low sugar. The term "low sugar" means a state where a saccharide is contained but the proportion of saccharide is relatively low. Accordingly, a saccharide-free state is not encompassed in the meaning of the low sugar. In a specific example of such an embodiment, the low sugar is a low glucose and the low glucose is not glucose free, for example. Typical examples of the low sugar include a composition in which saccharides are contained less than 1000 mg/L, and the like, for example. Examples of another solution of low sugar conditions include a condition where the content of saccharoids has been lowered to less than 1% in comparison with the conditions for saccharoids in general culture solutions that contain no additional saccharoid. In example, the amount of saccharides contained in the low sugar state solution may be specifically less than 1000 mg/L, preferably less than 500 mg/L, more preferably less than 200 mg/L, still more preferably less than 100 mg/mL.

In another embodiment, "low nutrient" means an amino acid-free state, that is, containing no amino acid. As a specific example of the low nutrient in such an embodiment, no essential amino acid is contained.

In the present disclosure, the term "low nutrient isotonic solution" means an isotonic solution which is low in nutrients. The low nutrient isotonic solution can be an isotonic solution containing a predetermined amount of carbohydrates, and/or an isotonic solution incapable of supplying essential amino acids, for example. The low nutrient isotonic solution is specifically an isotonic solution containing a predetermined amount of saccharides but containing no amino acid (especially, essential amino acid), an isotonic solution containing a predetermined amount of saccharides and a synthesis inhibitor for essential amino acids and the like, for example. The carbohydrate that can be contained in the low nutrient isotonic solution is typically saccharide. Examples of the saccharide may include but are not limited to, glucose, sucrose, maltose, fructose, galactose or the like, and can be appropriately selected depending on the desired type of cells or the like. The predetermined content of a saccharide may vary depending on the type of the contained saccharide or the required retention period (soaking time) of cells. In the case of glucose, for example, the viewpoint of the amount required for the life support of cells, the saccharide content may, for example, be approximately not less than 100 mg/L, approximately not less than 500 mg/L, approximately not less than 1000 mg/L, approximately not less than 1500 mg/L, approximately not less than 2000 mg/L, or the like. From the viewpoint of the maintenance of isotonicity, the saccharide content may, for example, be approximately not more than 50000 mg/L, approximately not more than 40000 mg/L, approximately not more than 30000 mg/L, approximately not more than 25000 mg/L, approximately not more than 20000 mg/L, approximately not more than 15000 mg/L, approximately not more than 10000 mg/L, approximately not more than 5000 mg/L, approximately not more than 4500 mg/L, or the like. Thus, the example of the range of glucose content may include any desired combinations of these upper limits and these lower limits, and may include, for example, but are not limited to, approximately 100 mg/L to 500000 mg/L, approximately 500 mg/L to 25000 mg/L, approximately 500 mg/L to 4500 mg/L, approximately 1500 mg/L to 4500 mg/L, approximately 500 mg/L to 1500 mg/L. It is possible for those skilled in the art to calculate the predetermined content according to the type of the contained saccharide.

Examples of the low nutrient isotonic solution may include those each prepared by adding a predetermined amount of carbohydrate to an isotonic solution known to have a composition containing without any carbohydrate nor any amino acid, such as saline, phosphate-buffered physiological saline, and ringer solution, in addition to isotonic solutions each known to have a composition containing a predetermined amount of saccharide but containing no amino acid, such as Hanks' balanced salt solution, Earl's balanced salt solution, and glucose isotonic solutions. As the predetermined amount of carbohydrate, 1000 mg/L to 4500 mg/L of glucoses is generally contained, for example, in the case of Hanks' balanced salt solution or Earl's balanced salt solution, or approximately 50000 mg/L of glucose is generally contained, for example, in the case of a glucose isotonic solution. In an embodiment, the term "low nutrient isotonic solution" does not include stock solutions existing known as cold storage solutions for organs, such as UW solution, Euro-Collins solution, and Hypothermosol®.

The low nutrient isotonic solution of the present disclosure may contain lactic acid. Thus, in an embodiment of the present disclosure, the low nutrient isotonic solution contains no lactic acid. In addition, the low nutrient isotonic solution of the present disclosure may contain pyruvic acid. Thus, in an embodiment of the present disclosure, the low nutrient isotonic solution contains no pyruvic acid. In addition, the low nutrient isotonic solution of the present disclosure may contain ascorbic acid. Thus, in an embodiment of the present disclosure, the low nutrient isotonic solution contains ascorbic acid. In addition, the low nutrient isotonic solution of the present disclosure may contain fatty acid. Thus, in an embodiment of the present disclosure, the low nutrient isotonic solution contains no fatty acid. In addition, the low nutrient isotonic solution of the present disclosure may contain calcium. Thus, in an embodiment of the present disclosure, the low nutrient isotonic solution contains calcium, for example, at a concentration preferably of approximately 1 mM to 2 mM, more preferably of approximately 1.2 mM to 1.8 mM. In addition, the low nutrient isotonic solution of the present disclosure may contain cholesterol. Thus, in an embodiment of the present disclosure, the low nutrient isotonic solution contains no cholesterol. In a preferred embodiment, the low nutrient isotonic solution contains none of lactic acid, pyruvic acid, fatty acid, and cholesterol, but contains ascorbic acid, and contains calcium, for example, at a concentration of approximately 1 mM to 2 mM, preferably of approximately 1.2 to 1.8 mM.

In this description, the term "carbohydrate" is a generic term for organic compounds formed of a saccharide such as a constituent unit, and encompasses saccharide derivatives and the like in addition to monosaccharides, oligosaccharides, and polysaccharides. In this description, the terms "saccharide" and "sugar" mean among carbohydrates, those which are metabolized by cells and converted to energy as well as their components typically represent monosaccharides and also include those which are degradated in the system and metabolized by cells.

In an aspect, the present disclosure relates to a method for modifying a sheet-shaped cell culture, containing at least two types of cells, and the method includes soaking the sheet-shaped cell culture in a low nutrient isotonic solution.

In accordance with an exemplary embodiment, when a sheet-shaped cell culture containing two or more types of cells, for example, a sheet-shaped cell culture containing skeletal myoblasts and fibroblasts, is soaked in a low nutrient isotonic solution, such as Hanks' balanced salt solution, a change occurs in the content ratio of the respective cell types whereby constituting the sheet-shaped cell culture, the sheet-shaped cell culture can be modified. As will be illustrated in Comparative example 1 to be discussed subsequently herein, the change in the content ratio is a phenomenon which does not occur in a cell mixture in a suspension state, and is a phenomenon which is specific to a sheet-shaped cell culture.

It has not been elucidated why a sheet-shaped cell culture is modified by the method of the present disclosure. As for the reason, without intending to be limited by theory, it may be considered that the formation of a cell culture into a sheet-shaped provides a viability improved over that of cells in a floating state, that the soaking in a low nutrient isotonic solution induces cells, which require much more nutrients for survival, to die easily so that the decreasing rate of cells varies from one type of mixed cells to another, that marked differences arise in variable cell count arise by soaking for a predetermined period.

The sheet-shaped cell culture for use in the method of the present disclosure contains at least two types of cells. Cells contained in the sheet-shaped cell culture include at least one type of cells among types of cells known in this technical field as cells constituting the above-described sheet-shaped cell culture. It can be preferred that all the cells contained in a sheet-shaped cell culture are selected from cells known in this technical field as cells to constituting the above-described sheet-shaped cell culture.

The sheet-shaped cell culture of the present disclosure, particularly the sheet-shaped cell culture, is useful for the medical treatment of various diseases, particularly diseases related to tissue abnormalities. Accordingly, in an embodiment, the sheet-shaped cell culture is to be used for the treatment diseases related to tissue abnormalities. Examples of tissues as targets for treatment include, but are not limited to, cardiac muscle, corneal, retina, esophagus, skin, joint, cartilage, liver, pancreas, gingiva, kidney, thyroid, skeletal muscle, middle ear, bone marrow, gastrointestinal tracts such as stomach, small intestine, duodenum, and large intestine, and the like. Examples of diseases on target disease for treatment include, but are not limited to, heart diseases (for example, myocardial lesions (cardiac infarction, and traumatic heart disease), and cardiomyopathy), corneal diseases (for example, corneal epithelial stem cell exhaustion disease, corneal damage (heat/chemical corrosion), corneal ulcer, corneal opacity, corneal perforation, corneal cicatrization, Stevens-Johnson's syndrome, and ocular pemphigoid), retinal diseases (for example, retinal pigmentary degeneration, and age-related macular degeneration), esophageal diseases (for example, prevention of esophageal inflammation/stricture after esophageal surgery (esophageal cancer removal)), skin diseases (for example, skin damages (injury, burn)), joint diseases (for example, deformans arthritis), cartilage diseases (for example, cartilage damage), liver diseases (for example, chronic liver disease, and the like), pancreas diseases (for example, diabetic), odontopathy (for example, periodontal disease), kidney diseases (for example, kidney failure, renal anemia, renal osteodystrophy), thyroid diseases (for example, thyroid gland hypofunction), muscular diseases (for example, muscular damage, myositis), middle ear diseases (for example, middle ear inflammation), and bone marrow diseases (for example, leukemia, aplastic anaemia, immunodeficiency disease).

Although the sheet-shaped cell culture can be used by applying the sheet-shaped cell culture to a tissue as a target for treatment to repair on regenerate the tissue, the sheet-shaped cell culture can be transplanted as a supply source of a biologically active substance, such as a hormone, to a site other than the tissue as the target for the treatment (for example, a subcutaneous tissue).

The sheet-shaped cell culture can be used for producing a pharmaceutical composition with a cell culture contained in the pharmaceutical composition. Such a pharmaceutical composition may also contain one or more of various additional ingredients, for example, a pharmaceutically acceptable carrier, an ingredient capable of heightening the viability, engraftment, function, and/or the like of the cell culture, another active ingredient useful for the treatment of a target disease, and the like. As for such additional ingredients, desired additional ingredients of known ingredients can be used, and those skilled in the art are cognizant of these additional ingredients. In addition, it is possible to use the pharmaceutical composition in combination with an ingredient capable of heightening viability, engraftment, function, and/or the like of the sheet-shaped cell culture, and/or another active ingredient useful for the treatment of the target disease.

In an embodiment of the present disclosure, the sheet-shaped cell culture is a cell culture in a sheet-shaped, which is to be used for the treatment of a heart disease. Examples of the sheet-shaped cell culture for use in the treatment of the heart disease, may include, but are not limited to, a sheet-shaped cell culture containing skeletal myoblasts, a sheet-shaped cell culture containing cardiac muscle cells (cardiomyocyte cells), a sheet-shaped cell culture containing vascular endothelial cells, a sheet-shaped cell culture containing mesenchymal stem cells and the like, with the sheet-shaped cell culture containing the skeletal myoblasts, the sheet-shaped cell culture containing the cardiac muscle cells (cardiomyocyte cells), and the sheet-shaped cell culture containing the vascular endothelial cells being preferred.

Examples of other constituent cells, which may also be contained in the sheet-shaped cell culture containing the skeletal myoblasts (desired cells), particularly the sheet-shaped cell culture, may include fibroblasts, vascular endothelial cells, and cells capable of differentiating into them (for example, stem cells, precursor cells). Examples of other constituent cells, which may also be contained in the sheet-shaped cell culture containing the cardiac muscle cells (cardiomyocyte cells) (desired cells), particularly the sheet-shaped cell culture may include, vascular endothelial cells, smooth muscle cells, and cells capable of differentiating into them (for example, stem cells, precursor cells). Examples of other constituent cells, which may be also be contained in the sheet-shaped cell culture containing the vascular endothelial cells (desired cells), particularly the sheet-shaped cell culture, may include skeletal myoblasts, fibroblasts, cardiac muscle cells (cardiomyocyte cells), and cells capable of differentiating into them (for example, stem cells, precursor cells). Examples of other constituent cells, which may also be contained in the sheet-shaped cell culture containing the mesenchymal stem cells (desired cells), particularly the sheet-shaped cell culture, may include precursor cells, adipocytes, macrophages, and vascular endothelial cells. Here, the term "desired cells" means main constituent cells in the sheet-shaped cell culture of the present disclosure, and in a cell culture for use in the treatment of a disease specifically means cells useful for the treatment of the disease.

According to the method of the present disclosure, it is possible to increase the purity of the desired cells by decreasing the number of other constituent cells in the sheet-shaped cell culture, particularly in the sheet-shaped cell culture. Thus, the method of the present disclosure can provide a sheet-shaped cell culture in which the purity of desired cells is high. In the case of a sheet-shaped cell culture, particularly a sheet-shaped cell culture, which contains, for example, skeletal myoblasts and fibroblasts, the use of the method of the present disclosure can lower the content of fibroblasts so that the purity of the skeletal myoblasts can be increased.

In a preferred embodiment of the present disclosure, the sheet-shaped cell culture, particularly the sheet-shaped cell culture, can include skeletal myoblasts and fibroblasts. In another preferred embodiment, the sheet-shaped cell culture, particularly the sheet-shaped cell culture, contains skeletal myoblasts, fibroblasts, and mesenchymal stem cells. In a further preferred embodiment, the sheet-shaped cell culture, particularly the sheet-shaped cell culture includes, no cells other than skeletal myoblasts, or fibroblasts, or cells differentiated from skeletal myoblasts or the fibroblasts. In a still further preferred embodiment of the present disclosure, the sheet-shaped cell culture, particularly the sheet-shaped cell culture, includes cardiac muscle cells (cardiomyocyte cells) and vascular endothelial cells. In an even further preferred embodiment, the sheet-shaped cell culture, particularly the sheet-shaped cell culture, includes no cells other than cardiac muscle cells, or vascular endothelial cells, or cells differentiated from vascular endothelial cells. In a still even further preferred embodiment of the present disclosure, the sheet-shaped cell culture, particularly the sheet-shaped cell culture, includes skeletal myoblasts, fibroblasts, and vascular endothelial cells. In a yet even further preferred embodiment, the sheet-shaped cell culture, particularly the sheet-shaped cell culture, includes no cells other than skeletal myoblasts, fibroblasts, or vascular endothelial cells, or differentiated from skeletal myoblasts, the fibroblasts, or the vascular endothelial cells.

In another preferred embodiment of the present disclosure, the sheet-shaped cell culture, particularly the sheet-shaped cell culture, includes mesenchymal stem cells and impurity cells of the mesenchymal stem cells. Here, the term "the impurity cells of the mesenchymal stem cells" means cells other than mesenchymal stem cells, which contaminate at the time of obtaining the mesenchymal stem cells. The impurity cells of mesenchymal stem cells differ depending on the origin of the mesenchymal stem cells. From an origin tissue, any of those skilled in the art can easily find the type of contaminated impurity cells. Known examples of the origin of mesenchymal stem cells, may include bone marrow, adipose tissue, umbilical cord, cord blood, peripheral blood, pulp tissue, placenta, synovial tissue, periodontal ligament, dermal tissue, endometrium, decidua vera, and the like. Examples of impurity cells in mesenchymal stem cells, may include, in the case of bone marrow-derived cells, precursor cells, adipocytes, macrophages, vascular endothelial cells and the like, and in the case of adipose tissue-derived cells, precursor cells, adipocytes, fibroblasts, vascular endothelial cells, and the like.

In an embodiment, the present disclosure provides a sheet-shaped cell culture, particularly a sheet-shaped cell culture, with skeletal myoblasts and fibroblasts being contained in the sheet-shaped cell culture, in which the content of the fibroblasts has decreased and the purity of the skeletal myoblasts has increased. The present disclosure provides a sheet-shaped cell culture, particularly a sheet-shaped cell culture, with cardiac muscle cells (cardiomyocyte cells) and cells other than cardiac muscle cells (cardiomyocyte cells) being contained herein, in which the content of cells other than cardiac muscle cells (cardiomyocyte cells) has decreased and the purity of cardiac muscle cells (cardiomyocyte cells) has increased. Non-limiting examples of cells other than cardiac muscle cells (cardiomyocyte cells) may include pluripotent stem cells, iPS cells, and undifferentiated cells derived from iPS cells. The present disclosure provides a sheet-shaped cell culture, particularly a sheet-shaped cell culture with cardiac muscle cells (cardiomyocyte cells), vascular endothelial cells and cells other than cardiac muscle cells (cardiomyocyte cells) on vascular endothelial cells being contained in the sheet-shaped cell culture, in which the purity of cells other than cardiac muscle cells (cardiomyocyte cells) or vascular endothelial cells has decreased and the purities of cardiac muscle cells (cardiomyocyte cells) and vascular endothelial cells have increased. Non-limiting examples of cells other than cardiac muscle cells (cardiomyocyte cells) or vascular endothelial cells may include pluripotent stem cells, iPS cells, and undifferentiated cells derived from iPS cells.

In an embodiment of the present disclosure, the sheet-shaped cell culture contains cells induced through differentiation from pluripotent stem cells including iPS cells. In such an embodiment, an unfavorable situation may arise because undifferentiated cells remain upon obtaining cells (for example, cardiac muscle cells (cardiomyocyte cells) or the like) through differentiation from pluripotent stem cells and there remaining undifferentiated cells involve a risk of tumorigenic transformation or the like. According to the method of the present disclosure, however, it is possible to decrease the content of such remaining undifferentiated cells. In addition, it is possible, for example, by adjusting the soaking time, to control the content of the desired cells (for example, cardiac muscle cells (cardiomyocyte cells)) within a desired range.

In a preferred embodiment of the present disclosure, the sheet-shaped cell culture includes cardiac muscle cells (cardiomyocyte cells) derived through differentiation from iPS cells. In such an embodiment, examples of other cells contained in the sheet-shaped cell culture, may include endothelial cells derived through differentiation from iPS cells, blood vessel-forming cells such wall cells and the like. In an embodiment, the sheet-shaped cell culture is a cell culture, preferably a sheet-shaped cell culture, which contains 30% to 70% of iPS-derived cardiac muscle cells (cardiomyocyte cells) (desired cells), 0.1% to 20% of iPS cell-derived vascular endothelial cells, and 1% to 40% of iPS cell-derived vascular wall cells. In the case of such a sheet-shaped, iPS cell-derived cardiac muscle cells culture, soaking in a low nutrient isotonic solution decreases the number of cells other than cardiac muscle cells as desired cells (cardiomyocyte cells) resulting in an improvement in the content of cardiac muscle cells (cardiomyocyte cells).

The iPS cell-derived cardiac muscle cells culture of the above-described embodiment may contain cardiac muscle cells, for example, at approximately not less than $5.0 \times 10^4$ cells/cm$^2$, preferably approximately not less than $1.0 \times 10^5$ cells/cm$^2$. In another embodiment, such cardiac muscle cells (cardiomyocyte cells), for example, may be contained at approximately not more than $5.0 \times 10^6$ cells/cm$^2$, preferably approximately not more than $2.0 \times 10^6$ cells/cm$^2$, more preferably approximately not more than $1.0 \times 10^6$ cells/cm$^2$. Thus, the number of cardiac muscle cells (cardiomyocyte cells) which can be contained in the sheet-shaped cell culture of the present disclosure may fall within the range defined by the desired one of the above-described upper limits and desired one of the above-described lower limits, for example, within $5.0 \times 10^4$ to $5.0 \times 10^6$ cells/cm$^2$, preferably $1.0 \times 10^5$ to $2.0 \times 10^6$ cells/cm$^2$ or the like. In a further embodiment, the number of such cardiac muscle cells (cardiomyocyte cells) may be $1.0 \times 10^5$ to $1.0 \times 10^6$ cells/cm$^2$ or the like.

In a preferred embodiment of the present disclosure, the low nutrient isotonic solution is Hanks' balanced salt solution. The composition of Hanks' balanced salt solution is known in this technical field as an isotonic solution containing glucose at the concentration of 1000 mg/L. Hanks' balanced salt solution is available as HBSS (+) containing divalent cations, such as magnesium and calcium, and also as HBSS (−) containing none of them, and HBSS (+) is more preferred in the present disclosure. HBSS (+) typically has the following composition: calcium chloride (anhydrous), 140 mg/L; magnesium chloride (hexahydrate), 100 mg/L; magnesium sulfate (heptahydrate), 100 mg/L; potassium chloride, 400 mg/L; potassium dihydrogenphosphate, 60 mg/L; sodium hydrogencarbonate, 350 mg/L; sodium chloride, 8000 mg/L; sodium hydrogenphosphate, 48 mg/L; and glucose, 1000 mg/L.

The low nutrient isotonic solution in the present disclosure may contain one or more additional ingredients each in an amount such that no adverse effect is imposed on the sheet-shaped cell culture. Examples of the additional ingredients may include, but are not limited to, for example, radical scavengers. Specific examples of the radical scavengers may include vitamins, such as vitamin C, vitamin E, and edaravone.

The sheet-shaped cell culture may be soaked at a temperature which can be appropriately selected in a range where no damage is caused on the sheet-shaped cell culture. In an embodiment, soaking is conducted at room temperature. In another embodiment, soaking is conducted under refrigerated condition, for example, at approximately 2° C. to 8° C. Accordingly, non-limiting examples of the temperature condition upon soaking may include approximately 2° C. to 40° C., approximately 2° C. to 35° C., approximately 2° C. to 30° C., approximately 2° C. to 25° C., approximately 2° C. to 20° C., approximately 2° C. to 15° C., approximately 2° C. to 10° C., approximately 2° C. to 8° C., approximately 2° C. to 4° C., approximately 8° C. to 40° C., approximately 10° C. to 40° C., approximately 15° C. to 40° C., approximately 20° C. to 40° C., approximately 25° C. to 40° C., approximately 30° C. to 40° C., approximately 35° C. to 40° C., approximately 8° C. to 35° C., approximately 8° C. to 30° C., approximately 8° C. to 25° C., approximately 15° C. to 40° C. and the like. In accordance with an exemplary embodiment, if a long soaking time is employed, a refrigerated condition is preferred from the viewpoint that damage on the sheet-shaped cell culture can be reduced.

The soaking time of the sheet-shaped cell culture is not particularly limited, insofar as the soaking time is in a range that no damage is imposed on the sheet-shaped cell culture. However, soaking for an excessively long time is not preferred because a soaking solution is low nutrient. Thus, examples of the upper limit of the soaking time may include, but are not limited to, not more than two days (48 hours), not more than three days (72 hours), not more than 100 hours, not more than five days (120 hours), not more than 150 hours, not more than one week (168 hours), not more than 200 hours, and the like. In accordance with an exemplary embodiment, the sheet-shaped cell culture needs to be kept soaked for a period required to exhibit the effects of modification of the sheet-shaped cell culture through the soaking. Thus, examples of the lower limit of the soaking time may include, for example, but are not limited to, not less than 48 hours, not less than 24 hours, not less than 12 hours, not less than 10 hours, not less than 8 hours, not less than 6 hours, and not less than 4 hours. Thus, the range of the soaking time for the sheet-shaped cell culture may be defined by the combination of desired one of above-described upper limits and desired one of above-described lower limits. Examples of the range of the soaking time may be, but are not limited to, 4 hours to 200 hours, 6 hours to 200 hours, 8 hours to 200 hours, 10 hours to 200 hours, 12 hours to 200 hours, 24 hours to 200 hours, 48 hours to 200 hours, 4 hours to 168 hours, 6 hours to 168 hours, 8 hours to 168 hours, 10 hours to 168 hours, 12 hours to 168 hours, 24 hours to 168 hours, 48 hours to 168 hours, 4 hours to 150 hours, 6 hours to 150 hours, 8 hours to 150 hours, 10 hours to 150 hours, 12 hours to 150 hours, 24 hours to 150 hours, 48 hours to 150 hours, 48 hours to 144 hours, 4 hours to 120 hours, 6 hours to 120 hours, 8 hours to 120 hours, 10 hours to 120 hours, 12 hours to 120 hours, 24 hours to 120 hours, 48 hours to 120 hours, 4 hours to 100 hours, 6 hours to 100 hours, 8 hours to 100 hours, 10 hours to 100 hours, 12 hours to 100 hours, 24 hours to 100 hours, 48 hours to 100 hours, 4 hours to 72 hours, 6 hours to 72 hours, 8 hours to 72 hours, 10 hours to 72 hours, 12 hours to 72 hours, 24 hours to 72 hours, 4 hours to 48 hours, 6 hours to 48 hours, 8 hours to 48 hours, 10 hours to 48 hours, 12 hours to 48 hours, and 24 hours to 48 hours.

In the soaking of the sheet-shaped cell culture in the low nutrient isotonic solution, in any desired combination above-described soaking conditions may be used. The soaking conditions may vary depending on the type of the sheet-shaped cell culture to be soaked the kind of the low nutrient isotonic solution, and those skilled in the art can appropriately select optimum conditions. If a sheet-shaped cell culture with skeletal myoblasts and fibroblasts contained in the sheet-shaped cell culture, is soaked in a low nutrient isotonic solution, for example, non-limiting examples of the soaking contains may include approximately 2° C. to 8° C. for approximately 4 hours to 200 hours in Hanks' balanced salt solution, approximately 2° C. to 8° C. for approximately 8 hours to 150 hours in Hanks' balanced salt solution, approximately 2° C. to 8° C. for approximately 12 hours to 120 hours in Hanks' balanced salt solution, approximately 2° C. to 8° C. for approximately 24 hours to 72 hours in Hanks' balanced salt solution, approximately 15° C. to 30° C. for approximately 4 hours to 200 hours in Hanks' balanced salt solution, approximately 15° C. to 30° C. for approximately 8 hours to 150 hours in Hanks' balanced salt solution, approximately 15° C. to 30° C. for approximately 12 hours to 120 hours in Hanks' balanced salt solution, approximately 15° C. to 30° C. for approximately 24 hours to 72 hours in Hanks' balanced salt solution, approximately 2° C. to 8° C. for approximately 4 hours to 200 hours in a low nutrient isotonic solution with glucose contained at 4500 mg/L, approximately 2° C. to 8° C. for approximately 8 hours to 150 hours in a low nutrient isotonic solution with glucose contained at 4500 mg/L, approximately 2° C. to 8° C. for approximately 12 hours to 120 hours in a low nutrient isotonic solution with glucose contained at 4500 mg/L, approximately 2° C. to 8° C. for approximately 24 hours to 72 hours in a low nutrient isotonic solution with glucose contained at 4500 mg/L, approximately 15° C. to 30° C. for approximately 4 hours to 200 hours in a low nutrient isotonic solution with glucose contained at 4500 mg/L, approximately 15° C. to 30° C. for approximately 8 hours to 150 hours in a low nutrient isotonic solution with glucose contained at 4500 mg/L, approximately 15° C. to 30° C. for approximately 12 hours to 120 hours in a low nutrient isotonic solution with glucose contained at 4500 mg/L, and approximately 15° C. to 30° C. for approximately 24 hours to 72 hours in a low nutrient isotonic solution with glucose contained at 4500 mg/L. Under these soaking conditions the content (purity) of skeletal myoblasts in the sheet-shaped cell culture is increased thereby providing a sheet-shaped cell culture more preferred on the treatment of a heart disease by transplant.

In an embodiment, the sheet-shaped cell culture is a sheet-shaped cell culture. In another embodiment, the sheet-shaped cell culture is formed on a culture substrate and then, without being separated, the formed sheet-shaped cell culture is soaked in a low nutrient isotonic solution. In this case, the low nutrient isotonic solution can be used as a medium to be employed upon separation. As a specific example of such an embodiment, a low nutrient isotonic solution is added to a sheet-shaped cell culture formed on a culture substrate, and the sheet-shaped cell culture is soaked in the low nutrient isotonic solution and the sheet-shaped cell culture is then cooled as; a cooled low nutrient isotonic solution is added to a sheet-shaped cell culture formed on a culture substrate and after separation, the sheet-shaped cell culture is soaked as it is, and is than collected provided to use.

In an embodiment, the sheet-shaped cell culture is soaked in a low nutrient isotonic solution in an intermediate stage during the formation of forming the sheet-shaped cell culture. In this case, it is possible to change from normal culturing conditions to the low nutrient conditions in the intermediate stage during the formation, or it is also possible to start culturing under the low nutrient conditions at the time point of the start of the formation. As further alternative, after the sheet-shaped cell culture is soaked for a certain time period, in isotonic solution, the post-soaking low nutrient state is changed the normal culturing conditions. The switching between the normal culturing conditions and the low nutrient state may be achieved, for example, by adding deficient ingredients, such as, for example, saccharide and amino acid to the low nutrient isotonic solution, or by replacing culture solution.

In another embodiment, the sheet-shaped cell culture is a sheet-shaped cell culture. After formed on a culture substrate, the sheet-shaped cell culture is separated from the culture substrate. After separated, the sheet-shaped cell culture is soaked in a low nutrient isotonic solution. A sheet-shaped cell culture is known to contract to a certain extent when separated from the culture substrate. The extent of such contraction varies depending, for example, on the types of cells constituting the sheet-shaped cell culture, their content ratio, and the forming conditions. If the sheet-shaped cell culture of the present disclosure is formed using a cell population which contains skeletal myoblasts and fibroblasts, the contraction rate, for example, of the sheet diameter is approximately 30%, approximately 40%, approximately 50%, approximately 60%, approximately 70%, or approximately 80%, or so. In an embodiment of the present disclosure, the separated (in other words, contracted) sheet-shaped cell culture may have an area of approximately not less than 1 $cm^2$, preferably approximately not less than 3 $cm^2$, more preferably approximately not less than 6 $cm^2$, still more preferably approximately not less than 10 $cm^2$.

In an embodiment of the present disclosure, the sheet-shaped cell culture is formed of a plurality of single layer sheet-shaped cell cultures stacked together. Such a stacked sheet-shaped cell culture can be formed by superposing separated single-layer sheet-shaped cell cultures together. As the sheet-shaped cell culture, a plurality of single layer sheet-shaped cell cultures can be soaked in a low nutrient isotonic solution and can then be superposed into a stacked from or a plurality of single layer sheet-shaped cell cultures are superposed into stacked form and can then be soaked in a low nutrient isotonic solution.

In another aspect of the present disclosure, a method for producing a sheet-shaped cell culture is provided.

The method of the present disclosure for producing a sheet-shaped cell culture includes the following steps (a) to (c):

(a) seeding a cell population, which contains a desired types of cells, preferably two or more types of cells on a culture substrate at a density capable of forming a sheet-shaped cell culture without substantial proliferation;

(b) incubating the seeded cell population so as to form the sheet-shaped cell culture; and (c) soaking the formed sheet-shaped cell culture in a low nutrient isotonic solution.

In the step (a), the cell population to be seeded contains one or more types of cells selected from the cells constituting the above-described sheet-shaped cell culture, preferably two or more types of cells selected from the cells forming the above-described sheet-shaped cell culture. The content percentage (purity) of cells of the most common type among the two or more types of cells forming the sheet-shaped cell culture, for example, may be not less than 50%, preferably not less than 60%, more preferably not less than 70%, still more preferably not less than 75% at the time of completion of the formation of the sheet-shaped cell culture. In an embodiment, the production method of the present disclosure further includes, before seeding the cells, a step of freezing the cell population and a step of thawing the frozen cell population. In this embodiment, the cell population obtained by the thawing may be seeded after subsequent proliferation of the cells. In a preferred embodiment, however, such a cell proliferation step is not included between the thawing step of the frozen cell population and the step (a). A sheet-shaped cell culture produced in such an embodiment is higher in activities such as, for example, cytokine productivity, engraftment ability, blood vessel induction ability, and tissue regeneration ability, than the sheet-shaped cell culture produced in the embodiment including the cell proliferation step between the thawing step of the frozen cell population and the step (a). Here, the expression "higher in activities" means, but is not limited to, that the activities are higher by, for example, not less than 5%, not less than 10%, not less than 20%, not less than 30%, not less than 40%, not less than 50%, not less than 60%, not less than 70%, not less than 80%, not less than 90%, not less than 100% in comparison with the corresponding activities of the comparison target sheet-shaped cell culture. In another preferred embodiment, a sheet-shaped cell culture of the present disclosure, which contains skeletal myoblasts, for example, includes the skeletal myoblasts at 60% to 99%. In further preferred embodiment, a sheet-shaped cell culture of the present disclosure, which contains cardiac muscle cells (cardiomyocyte cells), for example, includes the cardiac muscle cells (cardiomyocyte cells) at 50% to 70%.

In an embodiment of the present disclosure, as the cell population to be seeded, it is possible to use a cell population containing cells induced through differentiation from pluripotent stem cells, such as iPS cells. In such an embodiment, an unfavorable situation may arise because undifferentiated cells remain upon obtaining cells (for example, cardiac muscle cells or the like) from pluripotent stem cells and these remaining undifferentiated cells involve a risk of tumorigenic transformation. According to the method of the present disclosure, the content of such remaining undifferentiated cells can be decreased. In addition, for example, by adjusting the soaking time, the content of desired cells (for example, cardiac muscle cells (cardiomyocyte cells)) can be controlled within a desired range.

In another embodiment of the present disclosure, the cell population to be seeded may be a sheet-shaped cell culture or a cell population prepared from the sheet-shaped cell culture, the sheet-shaped cell culture containing one or more types of cells selected from the cells constituting the above-described sheet-shaped cell culture, preferably two or more types of cells selected from the cells constituting the above-described sheet-shaped cell culture. Specifically, the cell population to be seeded may be a spheroid or embryoid body itself, or a cell population obtained by dispersing such a cell aggregate. In such an embodiment, in addition to the sheet-forming step (b) to be described subsequently herein, a step may further be included to form intercellular adhesion for the formation of a spheroid or embryoid body to be seeded. As conditions for forming a sheet-shaped cell culture of spheroids, or embryoid bodies, methods known in this technical field can be used. Non-limiting example of such methods include Miki et al., Cell Stem Cell 16, 699-711, Jun. 4, 2015, WO2014/185358, and WO2017/038562.

The sheet-shaped cell culture produced by the production method of the present disclosure may preferably a sheet-shaped cell culture for use in the treatment of a heart disease. Thus, in a preferred embodiment of the present disclosure, the cell population to be seeded includes skeletal myoblasts and fibroblasts. In another preferred embodiment of the present disclosure, the cell population to be seeded includes cardiac muscle cells (cardiomyocyte cells) and vascular endothelial cells. In a further preferred embodiment of the present disclosure, the cell population to be seeded includes skeletal myoblasts, fibroblasts, and vascular endothelial cells.

The expression "a density capable of forming a sheet-shaped cell culture without substantial proliferation" means a cell density capable of forming a sheet-shaped cell culture when cultured with a culture solution of a non-proliferation system in which growth factors are not contained substantially. This seeding density is higher than the seeding density in a method that uses a growth factor-containing culture solution, and may be equal to or higher than a density at which cells reach a confluent state. Such a density is, for example, not less than $1.0 \times 10^5$ cells/cm$^2$ although not limited thereto. The upper limit of the seeding density is not restricted in particular, insofar as the formation of a cell culture is not impaired and cells do not proceed to differentiation. For example, the upper limit may be less than $3.4 \times 10^6$ cells/cm$^2$. In an embodiment, the expression "a density capable of forming a sheet-shaped cell culture without substantial proliferation of cells" is equal to or higher than a density at which the cells reach a confluent state, or higher than such a confluent-state density.

The expression "a density capable of forming a sheet-shaped cell culture without substantial proliferation of cells" means $1.0 \times 10^5$ to $3.4 \times 10^6$ cells/cm$^2$ in an embodiment, $3.0 \times 10^5$ to $3.4 \times 10^6$ cells/cm$^2$ in another embodiment, $3.5 \times 10^5$ to $3.4 \times 10^6$ cells/cm$^2$ in a further embodiment, $1.0 \times 10^6$ to $3.4 \times 10^6$ cells/cm$^2$ in a still another embodiment, $3.0 \times 10^5$ to $1.7 \times 10^6$ cells/cm$^2$ in an even further embodiment, $3.5 \times 10^5$ to $1.7 \times 10^6$ cells/cm$^2$ in a still even further embodiment, and $1.0 \times 10^6$ to $1.7 \times 10^6$ cells/cm$^2$ in a yet even further embodiment. The above-described ranges may include both the one of the upper limit and the lower limit insofar as the upper limit is less than $3.4 \times 10^6$ cells/cm$^2$. Thus, the above-described density may be, for example, $3.0 \times 10^5$ cells/cm$^2$ (inclusive) to $3.4 \times 10^6$ cells/cm$^2$ (exclusive), $3.5 \times 10^5$ cells/cm$^2$ (inclusive) to $3.4 \times 10^6$ cells/cm$^2$ (exclusive), $1.0 \times 10^6$ cells/cm$^2$ (inclusive) to $3.4 \times 10^6$ cells/cm$^2$ (exclusive), $1.0 \times 10^6$ cells/cm$^2$ (exclusive) to $3.4 \times 10^6$ cells/cm$^2$ (exclusive), or $1.0 \times 10^6$ cells/cm$^2$ (exclusive) to $1.7 \times 10^6$ cells/cm$^2$ (inclusive).

The culture substrate is not particularly limited, insofar as cells can form a sheet-shaped cell culture on the culture substrate, and a culture substrate commonly used in the technical field can be employed. Examples of such a culture substrate may include, but are not limited to, polyethylene, polypropylene, Teflon (registered trademark), polyethylene terephthalate, polymethyl methacrylate, nylon 6,6, polyvinyl alcohol, cellulose, silicon, polystyrene, glass, polyacrylamide, polydimethyl acrylamide, metals (for example, iron, stainless steel, aluminum, copper, and brass), and the like. The term "culture substrate" may embrace, in addition to a surface of a culture vessel (for example, the bottom surface of a vessel), and a surface of a cell-culturing scaffold.

To the surface of the culture substrate, one or more treatments may be applied bring about one or more advantages in the production of a sheet-shaped cell culture, including a treatment for providing increased adhesiveness to cells and a treatment for facilitating separation. Examples of such treatments may include, but are not limited to, a corona discharge treatment, an ultraviolet radiation treatment, a coating treatment with a hydrophilic compound such as collagen gel or a hydrophilic polymer, a coating treatment with an extracellular matrix, such as collagen, fibronectin, laminin, vitronectin, proteoglycan or glycosaminoglycan, or with a cell adhesion factor, such as a cadherin family, a selectin family, or an integrin family, for example, a coating treatment with a material whose physical property changes in response to stimuli, such as temperature, or light.

Usable examples of the material whose physical property changes in response to a stimulus, such as temperature or light, may include, but are not limited to, known materials, such as temperature responsive materials each composed of a homopolymer or copolymer of a (meth)acrylamide compound, an N-alkyl-substituted (meth)acrylamide derivative (for example, N-ethylarylamide, N-n-propylacrylamide, N-n-propylmethacrylamide, N-isopropylacrylamide, N-isopropylmethacrylamide, N-cyclopropylacrylamide, N-cyclopropylmethacrylamide, N-ethoxyethylacrylamide, N-ethoxyethylmethacrylamide, N-tetrahydrofurfurylacrylamide, or N-tetrahydrofurfurylmethacrylamide), an N,N-dialkylsubstituted (meth)acrylamide derivative (for example, N,N-dimethyl(meth)acrylamide, N,N-ethylmethylacrylamide, or N,N-diethylacrylamide), a (meth)acrylamide derivative having a cyclic group (for example, 1-(1-oxo-2-propenyl)pyrrolidine, 1-(1-oxo-2-propenyl)piperidine, 4-(1-oxo-2-propenyl)morpholine, 1-(1-oxo-2-methyl-2-propenyl)pyrrolidine, 1-(1-oxo-2-methyl-2-propenyl)piperidine, or 4-(1-oxo-2-methyl-2-propenyl)morpholine), or a vinyl ether derivative (for example, methyl vinyl ether); and light responsive materials each composed of a light absorbing polymer having azobenzene groups, a copolymer of a vinyl derivative of triphenyl methane leucohydrooxide and an acrylamide-based monomer, or an N-isopropylacrylamide gel containing spirobenzopyran (see, for example, JP 1990-211865A, and JP 2003-33177A). Application of a predetermined stimulus to such a material can change the physical property of the material, for example, the hydrophilic property or hydrophobic property of the material, and to promote the separation of the cell culture adhered on the material. Culture dishes coated with a temperature responsive material are commercially available (for example, UpCell™ CellSeed Inc.), and are usable in the production method of the present disclosure.

The above-described culture substrate may have various shapes. The production method of the present disclosure can be conducted in a vessel of a desired size and shape with a vessel having a flat shape being preferred. In addition, the area of the flat surface is not particularly limited, for example, the area of the flat surface may be approximately 1 cm$^2$ to approximately 200 cm$^2$, preferably approximately 2 cm$^2$ to approximately 100 cm$^2$, and more preferably approximately 3 cm$^2$ to approximately 50 cm$^2$.

In the step (b), the seeded cell population is subjected to sheet-forming culture to form a sheet-shaped cell culture. The term "sheet-forming culture" means that cells seeded on a culture substrate are cultured to form a sheet-shaped cell culture (specifically, formed into a sheet). The sheet-forming culture can be conducted by seeding cells, which can form a sheet-shaped cell culture on a culture substrate, culturing the sheet-shaped cell culture for a predetermined period under conditions, which allows the cells of the sheet-shaped cell culture to interact with one another including interconnecting of the cells to one another. The culture period is not particularly limited, insofar as the culture is sufficient for the formation of the sheet-shaped cell culture. If undifferentiated cells are contained in the seeded cell population, the predetermined period may preferably be not larger than the predetermined a period in which the cells moved otherwise proceed with differentiation. Thus, in this embodiment, the cells remain in an undifferentiated state during the culture period. The proceeding of the cells to differentiation can be evaluated with any method known by those skilled in the art. For example, in the case of skeletal myoblasts, it is possible to use the expression of MHC or the multinucleation of the cells as an index of differentiation.

Conditions for the formation of the sheet-shaped cell culture can be any desired conditions under which the adhesion between cells and a substrate or intercellular adhesion can be realized. Such desired conditions may include, but are not limited to, general cell culture conditions, for example. As such conditions, there is culturing at 37° C. under 5% $CO_2$, for example. Thus, the sheet-forming culture can be conducted at room temperature (for example, at the temperature around 37° C.). In addition, the culture period varies depending on the type of cells that form a sheet-shaped cell culture (the sheet-forming cells), from the viewpoint of providing a time sufficient to form the sheet-shaped cell culture. If the sheet-forming cells are skeletal myoblasts, the culture period may be, but is not limited to, for example, not less than 12 hours, not less than 16 hours, not less than 20 hours, not less than 24 hours, not less than 26 hours, not less than 28 hours, not less than 30 hours, not less than 32 hours, not less than 36 hours. From the viewpoint of preventing cell differentiation, the culture period may be, but is not limited to, for example, 48 hours or less, 44 hours or less, 40 hours or less, or 36 hours or less. Thus, as the culture period, the range defined by the combination of desired one of these upper limits and desired one of these lower limits can be exemplified. The culture period may be, but is not limited to, for example, 12 to 48 hours, 16 to 48 hours, 20 to 48 hours, 24 to 48 hours, 26 to 48 hours, 28 to 48 hours, 30 to 48 hours, 32 to 48 hours, 36 to 48 hours, 12 to 44 hours, 16 to 44 hours, 20 to 44 hours, 24 to 44 hours, 26 to 44 hours, 28 to 44 hours, 30 to 44 hours, 32 to 44 hours, 36 to 44 hours, 12 to 40 hours, 16 to 40 hours, 20 to 40 hours, 24 to 40 hours, 26 to 40 hours, 28 to 40 hours, 30 to 40 hours, 32 to 40 hours, 36 to 40 hours, 12 to 36 hour, 16 to 36 hours, 20 to 36 hours, 24 to 36 hours, 26 to 36 hours, 28 to 36 hours, 30 to 36 hours, or 32 to 36 hours. Further, in the case where the sheet forming cells are cardiac muscle cells (including iPS cell-derived cardiac muscle cells (cardiomyocyte cells)), the lower limit may be, but is not limited to, for example, not less than 24 hours, not less than 30 hours, not less than 36 hours, and the upper limit may be, but is not limited to, 48 hours or less, 72 hours or less, 96 hours or less, or 120 hours or less. Thus, as the culture period, the range defined by the combination of desired one of these upper limits and desired one of these lower limits can be exemplified. The culture period may be, but is not limited to, for example, 24 to 48 hours, 24 to 72 hours, 24 to 96 hours, 24 to 120 hours, 30 to 48 hours, 30 to 72 hours, 30 to 96 hours, 30 to 120 hours, 36 to 48 hours, 36 to 72 hours, 36 to 96 hours, or 36 to 120 hours. Those skilled in the art can select optimal conditions according to the type of the cells to be seeded. Non-limiting examples of the sheet-forming culture are described, for example, in JP 2007-528755T, JP 2010-081829A, JP 2010-226991A, JP 2011-110368A, JP 2011-172925A, and WO2014/185517.

The sheet-forming medium for use in the sheet-forming culture is not particularly limited, insofar as it can induce the sheet-forming culture of the cells. Usable examples may include, saline, various biological buffers (for example, PBS, and HBSS), solutions based on various cell-culturing basal media. Examples of such basal media may include, but are not limited to, DMEM, MEM, F12, DME, RPMI 1640, MCDB (MCDB 102, 104, 107, 120, 131, 153, 199 and so on), L15, SkBM, RITC 80-7, and DMEM/F12. Many of these basal media are commercially available, and their compositions are also known. It is possible to use such a basal medium with its standard composition being kept unchanged (for example, in just a commercially available state) or to change its composition appropriately as needed according to the cell type and the culturing conditions. Thus, the basal medium is not limited to one having a known composition but includes one with one or more added ingredients, removed, or increased or decreased in amount or amounts. The sheet-forming medium may contain one or more of additives, such as serum (for example, bovine serum such as fetal bovine serum, horse serum, and human serum), various growth factors (for example, FGF, EGF, VEGF, and HGF).

In addition, as described above, the cells are seeded at a density that does not allow the cells to proliferate. Unlike the existing method, it is thus possible to obtain a sheet-shaped cell culture of a desired size and shape in a short period, without waiting until the cell culture grows to the desired size. The size and shape of the sheet-shaped cell culture can be controlled as desired, for example, by adjusting the size and shape of the cell-adhering surface of a culture substrate, or disposing a frame of the desired size and shape on the cell-adhering surface of a culture vessel and culturing the cells in the culture vessel.

In an embodiment of the present disclosure, in the step (c), the formed sheet-shaped cell culture is soaked in a low nutrient isotonic solution. Thus, the sheet-shaped cell culture is soaked in a contracted state in the low nutrient isotonic solution. Details of such a soaking step reside in the recitation regarding the above-described modification method for the sheet-shaped cell culture.

In another embodiment, the method of the present disclosure further includes a step (c') in which the formed sheet-shaped cell culture is separated. This step (c') may be conducted either before or after the step (c). In the step (c'), it is possible to use, as a separation medium, a general culture medium or a low nutrient isotonic solution. If low nutrient isotonic solution is used as the separation medium, it is possible to conduct the step (c') directly after the formed sheet-shaped cell culture is soaked in the low nutrient isotonic solution in the step (c), or after separation in the step (c'), to soak the separated, sheet-shaped cell culture in the separation medium as it is, whereby the step (c) is conducted. In addition, the soaking of the sheet-shaped cell culture and the subsequent storage of the soaked, sheet-shaped cell culture may be conducted at room temperature or under refrigerated conditions, with the refrigerated conditions being preferred.

The separation is not particularly limited, insofar as the sheet-shaped cell culture can be separated from the culture substrate while its structure is retained. Any desired method known in this technical field can be used. Described specifically, it is possible to conduct the separation, for example, by an enzymatic treatment with a protease (for example, trypsin), a mechanical treatment by pipetting, physical separation from the use of culture substrate. In addition, if a culture substrate is used with a surface of the culture substrate coated with a material that changes in physical property in response to a stimulus, such as temperature and light, it is possible to detach the formed, sheet-shaped cell culture nonenzymatically by applying a predetermined stimulus. For example, a surface of the culture substrate can be coated with a temperature responsive material whose adhesiveness lowers at low temperatures, it is possible to separate the formed, sheet-shaped cell culture by adding a separation medium (which may be the same as the above-described sheet-forming culture medium) and then chilling (cooling) the culture substrate, or by adding a chilled (cooled) separation medium, in order to reduce its adhesiveness. Further, even if a chilled medium is added for separating the formed, sheet-shaped cell culture, the separation step itself may be conducted at room temperature (for example, a temperature around 37° C.), or under refrigerated conditions.

A sheet-shaped cell culture is known to contract to a certain extent when separated from a culture substrate. The extent of such contract varies according to the types and content ratio of the types of cells constituting the sheet-shaped cell culture, and the forming conditions of the sheet-shaped cell culture. If a cell population including skeletal myoblasts and fibroblasts is formed using similar sheet-forming culture as in the present disclosure, the contraction rate, for example, of the sheet diameter is approximately 30%, approximately 40%, approximately 50%, approximately 60%, approximately 70%, or approximately 80%. In an embodiment of the present disclosure, the separated (namely, contracted) sheet-shaped cell culture may have an area of approximately not less than 1 $cm^2$, preferably approximately not less than 3 $cm^2$, more preferably approximately not less than 6 $cm^2$, still more preferably approximately not less than 10 $cm^2$. Upon contraction of the separated sheet-shaped cell culture, the separated, sheet-shaped cell culture may be allowed to contract at room temperature (for example, a temperature around 37° C.), or under refrigerated conditions.

In addition, it is possible to add a washing step as desired in after the separation step (c). Such a washing step may also be conducted at room temperature (for example, a temperature around 37° C.) or under refrigerated conditions.

Details of such a separation step reside in the recitation regarding the above-described modification method for the sheet-shaped cell culture.

In an embodiment, the method of the present disclosure further includes, after the step (c'), a step (c") that a plurality of separated sheet-shaped cell cultures as defined above are stacked together. The step (c") may be conducted either before or after the step (c), insofar as conducted after the step (c'). Specifically, it is possible to conduct the separation and stacking after the soaking in the low nutrient isotonic solution to conduct, after the separation, the soaking in the low nutrient isotonic solution, and then the stacking, or to conduct, after the separation and stacking, the soaking of the sheet-shaped cell culture as a stacked product in the low nutrient isotonic solution.

In the present disclosure, the sheet-shaped cell culture can be transported in a state of being soaked in the low nutrient isotonic solution, insofar as soaking conditions such as temperature can be appropriately controlled. In addition, the sheet-shaped cell culture modified by the method of the present disclosure can be used for transplantation immediately after the sheet-shaped cell culture is taken out of the low nutrient isotonic solution. Thus, in an embodiment of the present disclosure, it is possible to produce a sheet-shaped cell culture, to soak the sheet-shaped cell culture in a low nutrient isotonic solution, to transport and store the sheet-shaped cell culture in this state, and then to take the sheet-shaped cell culture out for use.

The sheet-shaped cell culture of the present disclosure can be used for the production of a pharmaceutical composition, as described above. Thus, the present disclosure encompasses a method for treating the above-described various diseases with the sheet-shaped cell culture of the present disclosure.

The medical treatment method of the present disclosure includes a step of administering the sheet-shaped cell culture or an effective amount of a pharmaceutical composition containing the sheet-shaped cell culture to a subject who requires the sheet-shaped cell culture. Tissues and diseases to which the medical treatment method resides in the above-described recitation regarding the sheet-shaped cell cultures. Additionally, in such a medical treatment method, it is possible to use an ingredient, which increasing the viability, engraftment, function and/or the like of the sheet-shaped cell culture, one or more of other active ingredients useful for the treatment of a target disease and/or the like, together with the cell culture.

The various characteristic features described herein can be combined in various ways, and embodiments available from such combinations, inclusive of those not specifically described in the description herein, all fall within the scope of the present disclosure. In addition, those skilled in the art are well aware of the possibility of a multiplicity of various modifications without departing from the spirit of the present disclosure, and equivalents including such modifications are encompassed within the scope of the present disclosure. Accordingly, the embodiments described herein are merely exemplifications, and it is to be understood that these embodiments are not described with an intention to restrict the scope of the present disclosure. The present disclosure will hereinafter be specifically described by examples. However, the present disclosure is not limited to or the following by examples.

Example 1. Modification Test of Sheet-Shaped Cell Cultures (1) Preparation of Sheet-Shaped Cell Cultures The sheet-shaped cell cultures were prepared using skeletal myoblasts (with fibroblasts contained in the sheet-shaped cell cultures) prepared from a human skeletal muscle by a usual method (or conventional method). A cell mixture of human skeletal myoblasts and human fibroblasts suspended in a 20% human serum-containing DMEM/F12 medium (Thermo Fisher Scientific Inc.), was seeded at $3.7 \times 10^6$ cells/well on a temperature-responsive culture dish (UpCell® 12 well Multi-well, CellSeed Inc.), and was then subjected to the sheet-forming culture at 37° C. under 5% $CO_2$ for 12 hours to 26 hours. After the sheet-forming culture, the medium was removed, 700 µL/well of chilled HBSS (+) (Thermo Fisher Scientific Inc.) was added, and then the resultant was left still for 10 minutes. Then, gentile pipetting was conducted so as to separate the sheet-shaped cell cultures completely.

After the sheet-shaped cell cultures had been completely separated, HBSS (+) was removed, and a fresh supply of room-temperature HBSS (+) was added to conduct rinsing. Such a washing step was repeated four times. After HBSS (+) was removed, 1.55 mL/culture of a fresh supply of HBSS (+) was added and then the resultant was left still under conditions of 2° C. to 8° C.

(2) Evaluation of Content Ratio of Skeletal Myoblasts

With regard to the sheet-shaped cell cultures left still under the refrigerated conditions in preparation (1), the content ratio of skeletal myoblasts (hereinafter, referred to as "purity") was measured every 24 hours. After each formed sheet-shaped cell culture was dissociated with a trypsin-like protease, centrifugation was conducted and the supernatant was removed by decantation. After a 0.5% BSA-containing PBS solution was added to the resultant so as to rinse the cells, an anti-human CD56 antibody (Becton Dickinson) diluted 10 folds with a 0.5% BSA-containing PBS solution was added and mixed. As a control experiment, a control sample was provided in which a negative control antibody (Becton Dickinson) diluted 10 folds with a 0.5% BSA-containing PBS solution was added and mixed. Immediately after each antibody was mixed, the resultant was reacted in a cool dark place for approximately one hour and a 0.5% BSA-containing PBS solution was added so as to rinse the cells. Then, a 0.5% BSA-containing PBS solution was added and the resultant was subjected to an analysis. As the analysis, a flow cytometer (Becton Dickinson) was used so as to measure the proportion of antibody positive cells contained in the cells in which each antibody was mixed. In the measurement, a correction was conducted on the positive ratio of the negative control and 5,000 to 10,000 cells were analyzed. After the analysis, the purity was determined from a difference in the positive cell ratio of the cells in which each antibody was mixed.

The results are depicted in FIG. 1. As shown in FIG. 1, if soaked in HBSS (+) under refrigerated conditions, the purity of CD56-positive cells (specifically, skeletal myoblasts) increased, and reached approximately 90% in approximately 48 hours. The sheet-shaped cell culture was stored with the purity of approximately 90% remaining until a lapse of 144 hours. However, 216 hours later, the purity was suddenly dropped. As a reason for this drop, it is considered that skeletal myoblasts were unable to remain viable and began to die.

Comparative Example 1. Modification Test of Cells in Suspension

To a mixture of human skeletal myoblasts and human fibroblasts in a state not having been subjected to sheet-forming culture, 1.55 mL/well of HBSS (+) was added, and the resultant was left still under refrigerated conditions of 2° C. to 8° C. The purity of skeletal myoblasts was measured at the starting time of test and 72 hours later in a similar manner as in the above-described evaluation (2) of Example 1.

Figure 2:
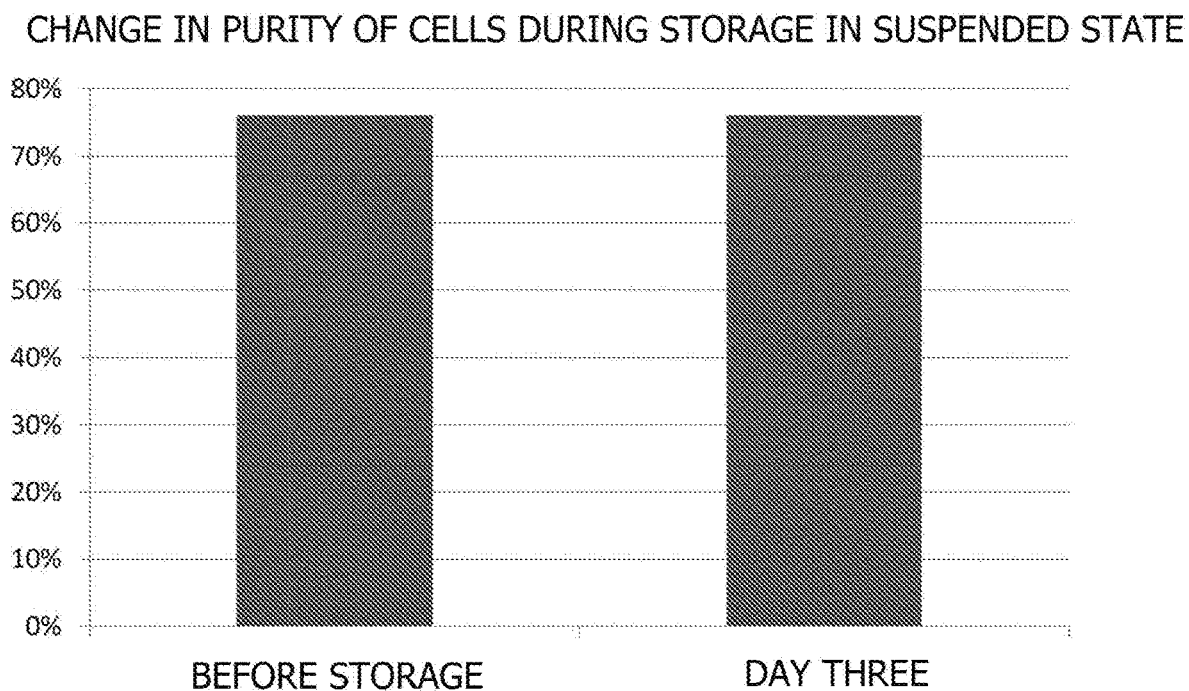
FIG. 2 is a graph depicting changes in the purity of skeletal myoblasts when an HBSS (+) suspension of human skeletal myoblasts and human fibroblasts was stored under the refrigerated conditions. On the third day after the start of storage, no change was observed in the purity of skeletal myoblasts.

The results were depicted in FIG. 2. In the case that no sheet-forming culture was conducted, it was unable to confirm any change in the purity of skeletal myoblasts.

The detailed description above describes method for modifying a sheet-shaped cell culture, a method for producing a sheet-shaped cell culture, the latter method including such a modification and the like. The invention is not limited, however, to the precise embodiments and variations described. Various changes, modifications and equivalents can be effected by one skilled in the art without departing from the spirit and scope of the invention as defined in the accompanying claims. It is expressly intended that all such changes, modifications and equivalents which fall within the scope of the claims are embraced by the claims.

What is claimed is:

1. A method for modifying a sheet-shaped cell culture containing at least two types of cells, one of the at least two types of cells being desired cell types that comprise myoblasts and the other of the at least two types of cells being constituent cell types that comprise fibroblasts, the method comprising:
changing a content ratio of the myoblasts and fibroblasts constituting the sheet-shaped cell culture so that the content ratio of the myoblasts over the fibroblasts is increased in the sheet-shaped cell culture; and the changing of the content ratio of the myoblasts and the fibroblasts so that the content ratio of the myoblasts over the fibroblasts is increased in the sheet-shaped cell culture occurs as a result of soaking the sheet-shaped cell culture in a low nutrient isotonic solution, the low nutrient isotonic solution being Hanks' balanced salt solution and the soaking the sheet-shaped cell culture occurring at a temperature from 2° C. to 8° C. and at a duration from 24 hours to 150 hours.

2. The method according to claim 1, wherein the myoblasts comprise skeletal myoblasts.

3. The method according to claim 1, wherein the sheet-shaped cell culture is a cell aggregate, an embryoid body, a spheroid, cells linked together into the shape of a sheet or a sheet-shaped cell culture that is adhered onto a culture substrate.

4. The method according to claim 3, further comprising:
separating the sheet-shaped cell culture from the culture substrate.

5. The method according to claim 4, wherein the sheet-shaped cell culture has contracted upon the separation of the sheet-shaped cell culture from the culture substrate.

6. The method according to claim 4, wherein the sheet-shaped cell culture has an area of not less than 6 cm' after the separation from the culture substrate.

7. The method according to claim 3, wherein the sheet-shaped cell culture includes a plurality of single layer sheet-shaped cell cultures stacked together.

8. A method for producing a sheet-shaped cell culture, the method comprising:
seeding a cell population on a culture substrate at a density that will form a sheet-shaped cell culture without proliferation, the cell population containing two or more types of cells, the two or more types of cells including one type of cell comprising myoblasts and another type of cell comprising fibroblasts;

forming the sheet-shaped cell culture by subjecting the seeded cell population to a sheet-forming culture;

increasing a ratio of the myoblasts over the fibroblasts in the sheet-shaped cell culture by soaking the formed sheet-shaped cell culture in Hanks' balanced salt solution; and the soaking of the formed sheet-shaped cell culture in the Hanks' balanced salt solution includes soaking the formed sheet-shaped cell culture in the Hanks' balanced salt solution for 24 hours to 150 hours at 2° C. to 8° C.

9. The method according to claim 8, further comprising:
separating the formed sheet-shaped cell culture from the culture substrate before the soaking of the formed sheet-shaped cell culture in the Hanks' balanced salt solution.

10. The method according to claim 9, further comprising:
separating the formed sheet-shaped cell culture from the culture substrate after the soaking of the formed sheet-shaped cell culture in the Hanks' balanced salt solution.

11. The method according to claim 10, wherein the sheet-shaped cell culture contracts upon the separation from the culture substrate.

12. The method according to claim 11, wherein the separated sheet-shaped cell culture or the produced sheet-shaped cell culture has an area of not less than 6 cm$^2$.

13. The method according to claim 9, further comprising:
stacking a plurality of the separated sheet-shaped cell cultures together.

14. The method according to claim 10, further comprising:
stacking a plurality of the formed sheet-shaped cell cultures together.

15. A method for producing a sheet-shaped cell culture, the method comprising:
seeding a cell population on a culture substrate at a density that will form a sheet-shaped culture without proliferation, the cell population containing myoblasts as a desired type of cells and also containing fibroblasts;

subjecting the seeded cell population to sheet-forming culture to form a sheet-shaped cell culture;

separating the formed sheet-shaped cell culture from the culture substrate to obtain a separated sheet-shaped cell culture; and increasing a ratio of the myoblasts relative to the fibroblasts in the separated sheet-shaped cell culture by soaking the separated sheet-shaped cell culture in Hanks' balanced salt solution for 24 hours to 150 hours at 2° C. to 8° C. so that the ratio of the myoblasts to the fibroblasts in the separated sheet-shaped cell culture after the soaking in the Hanks' balanced salt solution for 24 hours to 150 hours at 2° C. to 8° C. is greater than the ratio of the myoblasts to the fibroblasts in the separated sheet-shaped cell culture before the soaking of the separated sheet-shaped cell culture in the Hanks' balanced salt solution.

16. The method according to claim 15, further comprising:
separating the sheet-shaped cell culture from the culture substrate after the soaking of the sheet-shaped cell culture in the Hanks' balanced salt solution.

17. The method of claim 8 wherein the sheet-shaped cell culture is soaked in the Hanks' balanced salt solution for 24 hours to 72 hours.

18. The method of claim 15 wherein the separated sheet-shaped cell culture is soaked in the Hanks' balanced salt solution for 24 hours to 72 hours.

19. The method of claim 1, wherein the concentration of the desired cell types that comprise myoblasts is not less than 50% of the sheet-shaped cell culture after the soaking step.

20. The method of claim 1, wherein the concentration of the desired cell types that comprise myoblasts is not less than 60% of the sheet-shaped cell culture after the soaking step.

21. The method of claim 1, wherein the sheet-shaped cell culture is soaked in the low nutrient isotonic solution for 24 hours to 72 hours.

22. The method of claim 1, wherein the low nutrient isotonic solution contains a radical scavenger, the radical scavenger being vitamin C, vitamin E or edaravone.

23. The method of claim 8, wherein the Hanks' balanced salt solution contains a radical scavenger, the radical scavenger being vitamin C, vitamin E or edaravone.

24. The method of claim 15, wherein the Hanks' balanced salt solution contains a radical scavenger, the radical scavenger being vitamin C, vitamin E or edaravone.

* * * * *